United States Patent [19]
Peyton

[11] 4,221,961
[45] Sep. 9, 1980

[54] ELECTRONIC BOTTLE INSPECTOR HAVING PARTICLE AND LIQUID DETECTION CAPABILITIES

[75] Inventor: John J. Peyton, Santa Barbara, Calif.

[73] Assignee: Industrial Automation Corporation, Goleta, Calif.

[21] Appl. No.: 953,865

[22] Filed: Oct. 23, 1978

[51] Int. Cl.² ............................................. G01N 21/24
[52] U.S. Cl. ................................. 250/223 B; 250/341
[58] Field of Search ........................... 250/223 B, 341; 356/240; 209/524, 526

[56] References Cited

U.S. PATENT DOCUMENTS 4,121,103  10/1978  Calhoun .

OTHER PUBLICATIONS

Food Processing, Mar. 1978, pp. 52–53.

Primary Examiner—David C. Nelms
Assistant Examiner—Darwin R. Hostetter
Attorney, Agent, or Firm—Blakely, Sokoloff, Taylor & Zafman

[57] ABSTRACT

An electronic bottle inspector having particle and liquid detection capabilities through the use of sensing systems in the visible and infra-red light range. For particle inspection in the visible light range, light from a source, typically an incandescent source passing through the bottom of a bottle, is focused above the neck of the bottle to present an image of the bottom of the bottle on a rotating scanner characterized by a generally non-reflective background having one or more reflecting segments thereon. The scanner rotates at high speed so that the reflecting segment or segments scans the image focused thereon, with at least the reflective segments being contoured so the light falling thereon from the respective portion of the bottle bottom image is focused onto a detector. The particulate matter on the bottom of the bottle will block the light, creating a dip in detector output when that portion of the image is scanned. For liquid detection one or more holes are provided through the non-reflective portions of the scanner, with an infra-red detector being located therebehind to detect the infra-red radiation passing through the holes. Filtering of the light received by the detector allows peaking of the sensitivity of the system around one of the absorption bands of the liquid, with a drop in AC coupled amplitude of the infra-red detector providing an indication of the presence of the liquid.

18 Claims, 7 Drawing Figures

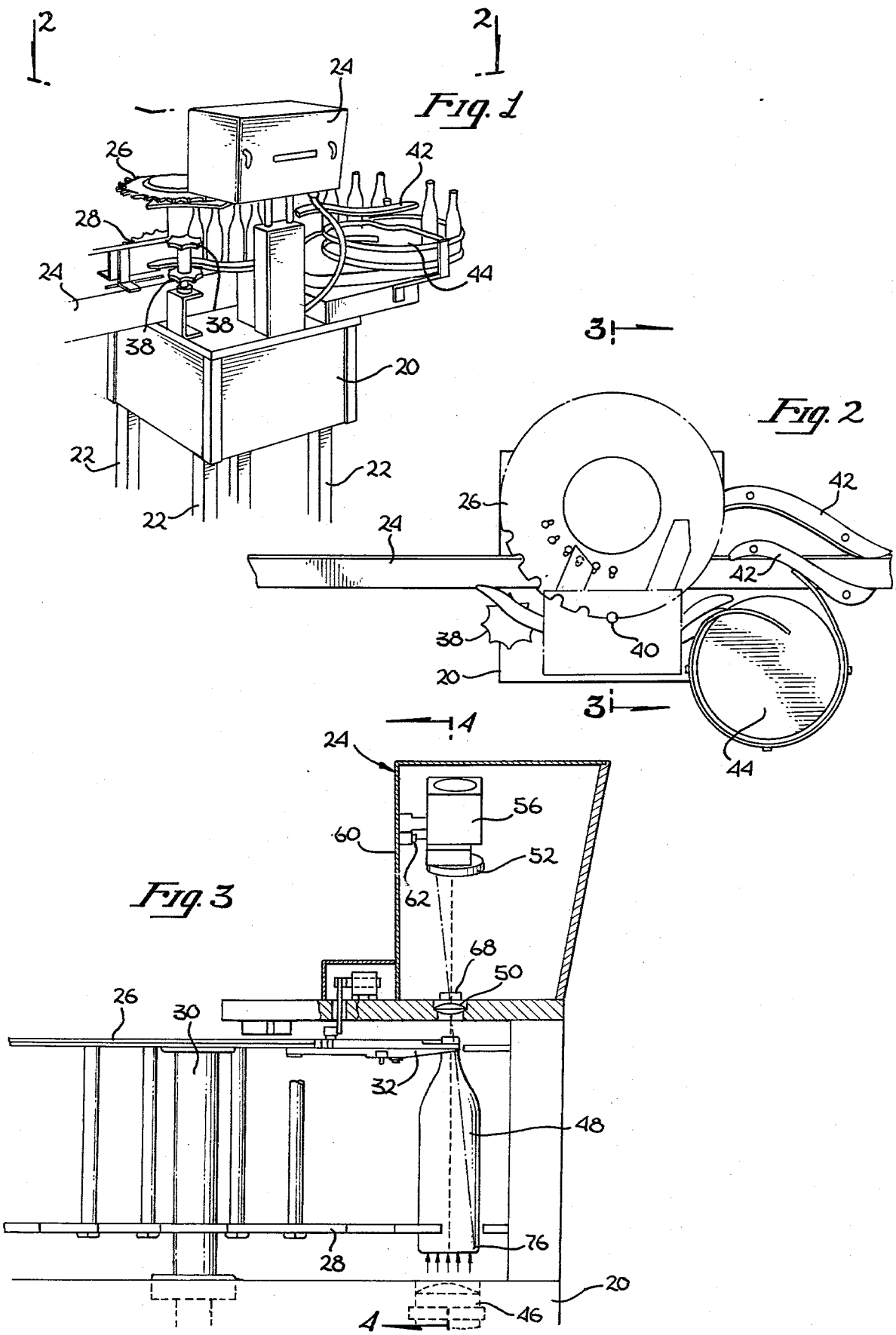

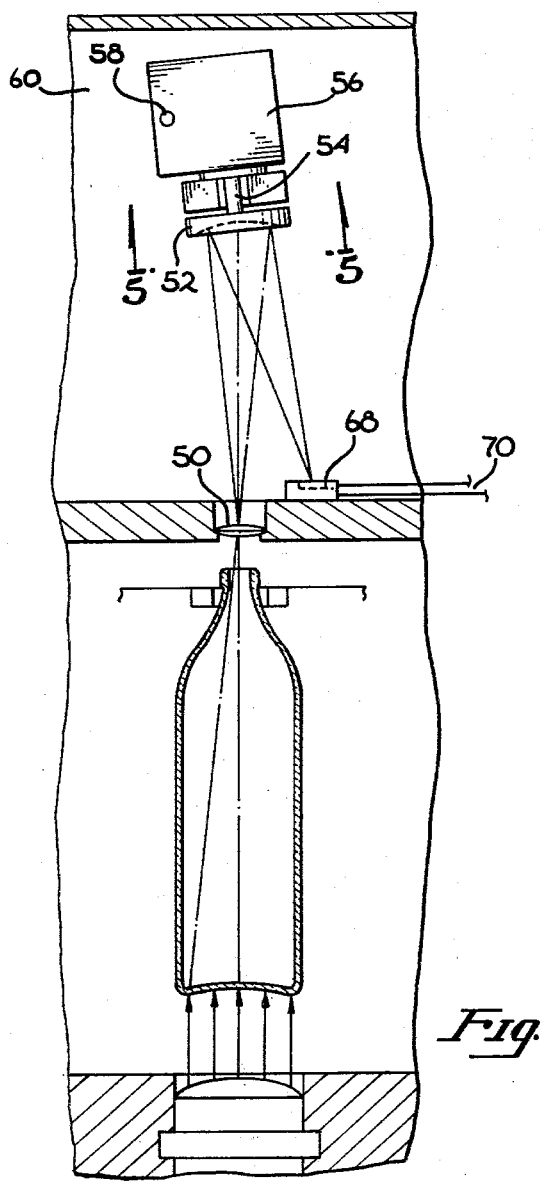
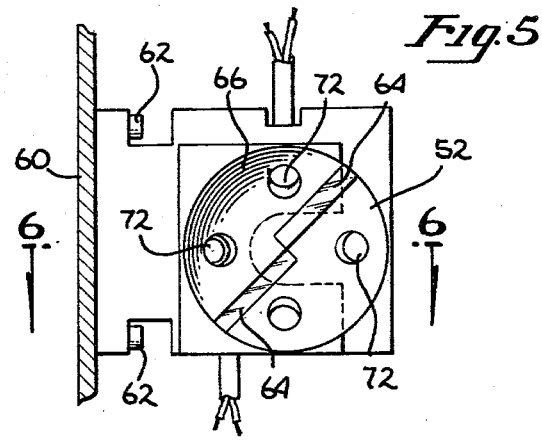
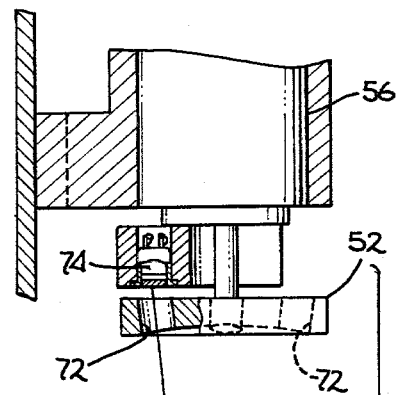
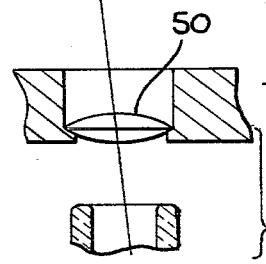
Fig. 4
Fig. 5
Fig. 6

ELECTRONIC BOTTLE INSPECTOR HAVING PARTICLE AND LIQUID DETECTION CAPABILITIES

BACKGROUND OF THE INVENTION

1. Field of the Invention

The present invention relates to the field of inspection equipment and more particularly to equipment for automatically detecting the presence of certain liquids and foreign objects in containers.

2. Prior Art

Electronic bottle inspectors for inspecting the interior of empty bottles for opaque foreign matter are well known in the prior art. Examples of such prior systems include those disclosed in U.S. Pat. Nos. 3,133,640 and 3,415,370. The latter patent is of particular interest as the present invention comprises a modification of a prior art system very similar to that disclosed in that patent. Such incorporation systems are generally characterized by a means of support of the bottle to be inspected from the side thereof with a light source, frequently an incandescent light source, below the bottle to direct light through the bottom thereof. Light passing through the bottom of the bottle and upward through the neck of the bottle is generally focused thereabove to provide an image of the bottom of the bottle, with some form of scanner or sensor array for sensing different portions of the image to determine relative light and dark areas, the dark areas, of course, representing the presence of opaque objects.

In the system of U.S. Pat. No. 3,415,370 the light passing through the bottom of the bottle and upward through the neck is focused by a lens thereabove onto the face of a rotating scanner, characterized by a concave surface having a non-reflective background with a single mirror segment thereon for sweeping the image focused onto the scanner. The axis of rotation of the scanner is inclined somewhat to the axis of the bottle so that the portion of the image reflected by the reflective portion of the scanner, being focused by the concave curvature thereon, is focused onto a detector displaced somewhat to the side of the focusing lens. The system of that patent also incorporates a neck inspection feature which could be utilized with the present invention, though in the preferred embodiment is not.

Equipment generally in accordance with U.S. Pat. No. 3,415,370, though not incorporating the neck inspection feature, has been manufactured for a number of years by Industrial Automation Corporation of Santa Barbara, California, assignor of the present invention. In that equipment a pair of approximately diametrically opposed mirror segments are utilized on the rotating scanner, and a bottle support mechanism generally in accordance with U.S. Pat. No. 3,975,260 is utilized.

The infra-red radiation absorption characteristics of water and water vapor are well known. (See for example, U.S. Pat. Nos. 2,703,844 and 3,021,427 and 3,089,382 and 3,153,722, and also Wood, the review of Scientific Instruments, Vol. 29, No. 1, pages 36–41, January 1958.) These absorption characteristics have been used to detect the presence or absence of a liquid at a particular level in a container, such as in U.S. Pat. No. 3,225,191, and to measure the relative amounts of water in containers such as in U.S. Pat. No. 2,321,900. The fact that infra-red energy may pass through containers which are relatively opaque to visible light is disclosed in the last stated patent, as well as U.S. Pat. No. 2,945,588. Other patents utilizing the absorption characteristics of water for detecting purposes includes U.S. Pat. No. 3,150,264 and No. 3,043,956, and for the detection of foreign matter in liquids using infra-red energy in U.S. Pat. No. 2,132,447.

Finally a system for inspection of empty beverage bottles is described starting on pages 52 and 53 of Food Processing, March, 1978. In accordance with that disclosure the bottom of a bottle is inspected from above for contaminants utilizing a dual inspection system comprised of superimposed radial and raster scanners. A beam splitter diverts a portion of the light gathered from the bottle bottom by the lens system and directs it to the raster scanner that gives uniform inspection over the center portion of the container. A coaxial radial scanner receives the remainder of the light and processes a portion of it to scan the outer portion of the container. The coaxial radial scanner system allows part of the light to pass on to the residual liquid detector that uses an infra-red scanner to detect the presence of minute amounts of water in the bottle. It is unknown at this time whether this system constitutes prior art, i.e. has priority of invention over the present invention.

BRIEF SUMMARY OF THE INVENTION

An electronic bottle inspector having particle and liquid detection capabilities through the use of sensing systems in the visible and infra-red light range. For particle inspection in the visible light range, light from a source, typically an incandescent source passing through the bottom of a bottle, is focused above the neck of the bottle to present an image of the bottom of the bottle on a rotating scanner characterized by a generally non-reflective background having one or more reflecting segments thereon. The scanner rotates at high speed so that the reflecting segment or segments scans the image focused thereon, with at least the reflective segments being contoured so that light falling thereon from the respective portion of the bottle bottom image is focused onto a detector. The particulate matter on the bottom of the bottle will block the light, creating a dip in detector output when that portion of the image is scanned. For liquid detection one or more holes are provided through the non-reflective portions of the scanner, with an infra-red detector being located therebehind to detect the infra-red radiation passing through the holes. Filtering of the light received by the detector allows peaking of the sensitivity of the system around one of the absorption bands of the liquid, with a drop in AC coupled amplitude of the infra-red detector providing an indication of the presence of the liquid.

BRIEF DESCRIPTION OF THE DRAWINGS

FIG. 1 is a perspective view of an electronic bottle inspector incorporating the present invention.

FIG. 2 is a view taken along line 2—2 of FIG. 1.

FIG. 3 is a view taken along line 3—3 of FIG. 2.

FIG. 4 is a view taken along line 4—4 of FIG. 3.

FIG. 5 is a view taken along line 5—5 of FIG. 4.

FIG. 6 is a side view of the scanner taken on an expanded scale to illustrate the location of the infra-red detector relative to the scanner.

DETAILED DESCRIPTION OF THE INVENTION

Figure 7:
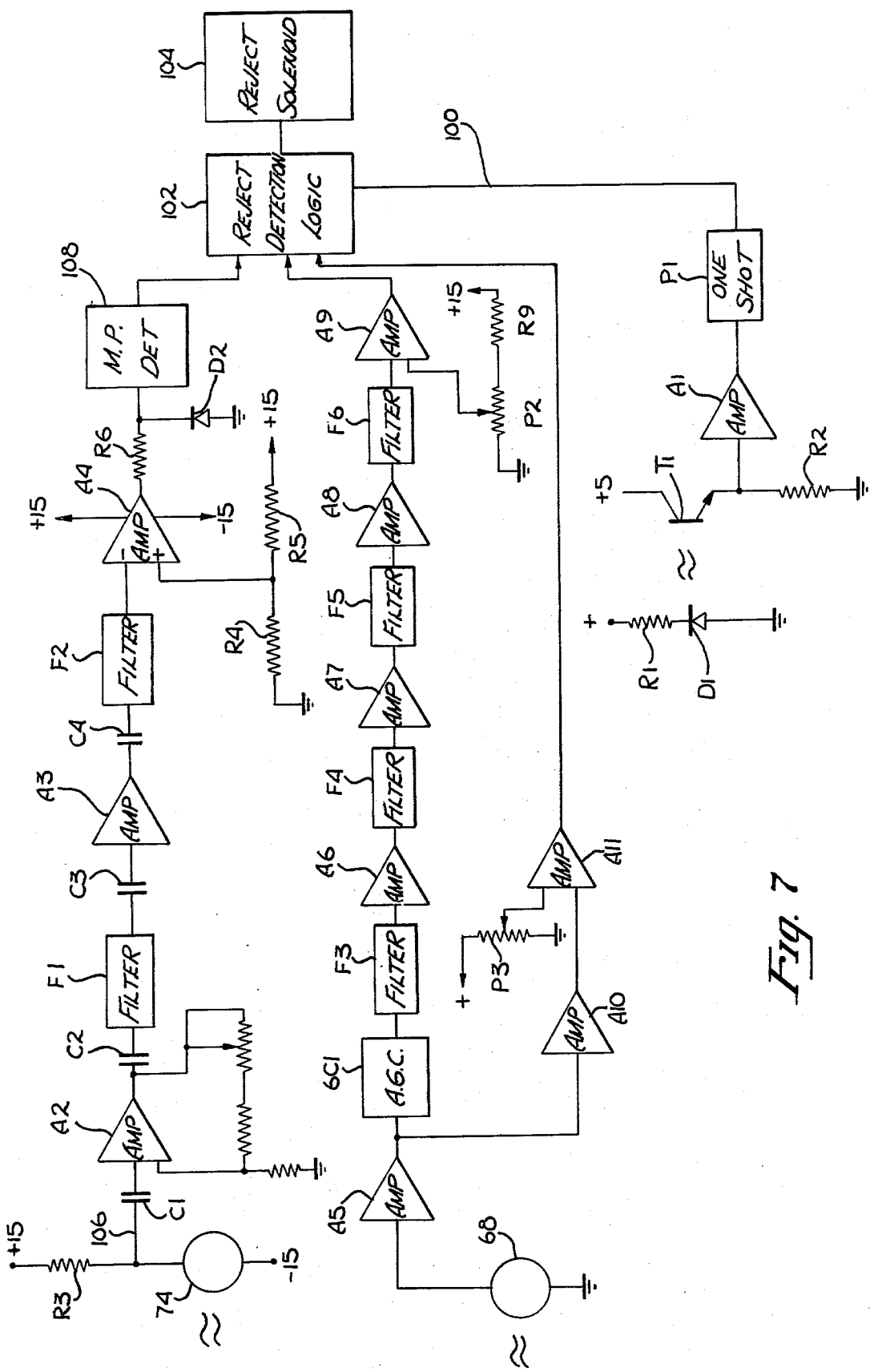
FIG. 7 is a block diagram of the electronics for providing reject signals upon the occurrence of a localized opaque obstruction in a bottle bottom, a distributed obstruction in the bottle bottom and/or a water-based solution.

First referring to FIG. 1, a perspective view of an electronic bottle inspector which may incorporate the present invention may be seen. The bottle inspector is characterized by a base 20 supported on legs 22 and in turn supporting an inspection head thereabove. As may be seen in greater detail in FIGS. 2 and 3 also, a supply conveyor 24 supplies bottles to the inspection machine, which bottles are picked up by rotating starwheel assembly comprising an upper starwheel 26 and a lower starwheel 28 supported on a central shaft 30 supported by the base 20. The individual bottles are gripped by the neck thereof by clamps 32 (see FIG. 3) to support the bottles from the side, the bottles being further confined by guides 34 and 36. Also a pair of idler starwheels 38 are provided adjacent the transition between the supply conveyor 24 and the starwheels 26 and 28 to further guide the bottles in that region. The bottles pass under the inspection station or position 40 at which time they are inspected by the inspection head 24, proceeding to the delivery guides 42 to be redeposited on the conveyor 24 if they pass inspection, or to be sooner delivered to rejected bottle storage coral 44 if the bottles do not pass inspection. These aspects of the system incorporating the present invention are generally in accordance with the disclosure of U.S. Pat. No. 3,975,260 assigned to the assignee of the present invention.

Now referring more specifically to FIGS. 3, 4 and 5, various details of the inspection system for inspecting bottles using visible light to detect opaque foreign matter therein may be seen. FIG. 3 is a view taken in partial cross-section through the inspection position 40 and the axis of rotation of the main starwheels, as shown by the section line 3—3 in FIG. 2. FIG. 4, on the otherhand, is a view also taken through the inspection position, though perpendicular to the section of FIG. 3, as illustrated by the section lines 4—4 of FIG. 3. FIG. 5 is a view looking directly into the face of the scanner taken along line 5—5 of FIG. 4. An incandescent light source 46 is disposed immediately below the inspection position 40, projecting relatively diffuse light toward the bottom of the bottle 48 at the inspection position. The light passing through the bottom of the bottle and out through the neck thereof is focused by a lens 50 onto the face of a rotating scanner head 52 supported on shaft 54 of motor 56 and rotated at high speed. The motor 56 (perhaps more accurately the motor mounting bracket as the motor itself, of conventional design, is housed therein and retained in position by clamp screw 58,) is fastened to the back wall 60 of the inspection head 24 by screws 62. The scanner head 52 is provided with a pair of reflecting approximately radially disposed sections 64 on an otherwise generally non-reflecting background 66. Thus, only the portion of the image of the bottom of the bottle which falls on the reflective segments 64 will be reflected by the scanner, the segments effectively sweeping or scanning the image at high speed because of the rotation of the scanner. The scanner surface or at least a portion of the surface containing the reflective elements 64 is generally spherical so as to focus the light reflected by the reflective element down to a detector 68 which provides an electrical signal on lines 70 which at any instant is proportional to the intensity of the light in the relatively small portions of the bottle image being reflected by the reflective segments 64 on the scanner. This signal, relatively uniform for a clean bottle, is continuously monitored by appropriate electronics to detect rates of changes of the signal indicative of a region of the image of low light intensity caused by an opaque object in the corresponding area of the bottle. The optical inspection system just described is similar to that described in U.S. Pat. No. 3,145,370 and has been utilized in electronic bottle inspectors manufactured by Industrial Automation Corporation of Santa Barbara, Calif. for many years.

The modification of the foregoing equipment to incorporate the present invention will now be described. It will subsequently be seen that the modification is particularly simple and interfaces extremely well with the scanner system just described. In particular, in the preferred embodiment, four equally spaced holes 72 are provided through the face of the scanner (see FIGS. 5 and 6) and an infra-red radiation sensor 74 is mounted therebehind. In the preferred embodiment the holes 72 are each positioned at a fixed radius on the scanner representing approximately 70% of the radial extent of the reflective portions. Furthermore the detector 74 is preferably located at a position generally radially inward with respect to the axis of the shaft 30 defining the axis of the rotary transport system moving the bottles in a circular arc past the inspection station. With such a detector location the infra-red energy passing through the openings in the scanner 52 and falling on the detector 74 is infra-red energy passing through a region of the bottom of the bottle being inspected approximately radially outward from the axis of the rotary transport system, i.e., in approximately region 76 shown in FIG. 3. In operation the centrifugal force on the wash water, caustic solution or any other liquid in the bottle will force that liquid outward to approximately position 76 shown in FIG. 3 so that the infra-red detector 74 is in effect viewing the portion of the bottle bottom most likely to be covered with the fluid. In that regard, it will be noted that the axis of the scanner, i.e. the axis of the motor shaft 54 about which the scanner rotates at high speed, is inclined with respect to the bottle being inspected as shown in FIG. 4 so that the reflected segment 64 reflects the portions of the visual image to the detector 68 located somewhat to the side of the axis of lens 50 and the bottle 48 being inspected. While this inclination obviously could be in any desired direction depending on the location of detector 68, in the preferred embodiment the inclination is achieved by the slight rotation of the motor housing about a radial axis of the rotary transport system. Accordingly, in this embodiment the projection of the scanner shaft 54 axis in the view of FIG. 6 is aligned with the lens and the bottle being inspected.

It was previously mentioned that the scanner 52 is located substantially at the focal plane of the image of the bottom of a bottle so that the reflective segments of the scanner scan the image on rotation thereof. Assuming the infra-red image has substantially the same focal point (though not a specific requirement) the portion of the infra-red image received by the detector 74 will in general not be well focused. However, this is of little consequence as the only sweeping of the infra-red image occurs not as a result of the rotating scanner but instead merely as a result of the motion of the bottle past the inspection position. Accordingly the detector 74 is in general responding to the level of the infra-red radiation incident thereto which will come generally from region 76 of FIG. 3, as opposed to responding to sharply focused portions of the infra-red image.

Now referring to FIG. 7, a block diagram of the electronics used for signal processing in the preferred embodiment may be seen. In the previous description, specifically with respect to FIG. 2, an inspection position 40 immediately under the inspection head was identified. In reality, however, a moving bottle is inspected by the stationary inspection head so that the bottle and the starwheel supporting the bottle actually move through a small arc during the relatively short inspection period. In the preferred embodiment the scanner rotates at approximately 12,000 rpm so that the bottle bottom may be quickly scanned before false signals might be derived from the edges of the bottle. Thus, as a bottle approaches position 40 (FIG. 2), a mechanical reference on the starwheel assembly trips the light beam from the light emitting diode D1 in the resistor R1 and photodiode D1 combination. This is detected by photo transistor T1, the combination of the photo transistor and resistor R2 providing a signal to a trigger amplifier A1 to fire one shot pulse generator P1 (a monostable device) to provide a pulse on line 100 representing the initiation and duration of the inspection period for any particular bottle. In the preferred embodiment the one shot P1 provides a pulse width of approximately 6 milliseconds, representing approximately 1.2 revolutions of the scanner during the alotted inspection time window. This signal is used by the reject detection logic 102 to effectively enable any of three specific reject signals (to be subsequently described in detail) to actuate the reject solenoid 104, corresponding to the solenoid 62 of U.S. Pat. No. 3,975,260. (In FIG. 7 and in the descriptions to follow with respect thereto, the key aspects of the signal processing are shown and described for exemplary purposes, though other aspects of the signal processing well known in the art, such as voltage level shifting to allow conventional logic levels for the reject detection logic 102, signal inversion to allow use of conventional logic, etc. are not shown, but are presumed to be well known and included in the reject detection logic 102.)

The infra-red detector 74 (see also FIGS. 3 and 4) is a photoconductor coupled in series with resistor R3 between ±15 V D/C power supplies. The signal therefrom on line 106 is A/C coupled by capacitor C1 to amplifier A2. The output of amplifier A2 is successively filtered by a filter F1, amplified by amplifier A3, filtered by filter F2 and applied to one input of amplifier A4 operated as a comparator, the various amplifiers and filters being coupled by capacitors C2, C3 and C4. In the preferred embodiment the filters F1 are active filters having an 800 Hz bandpass, so that the signal out of filter F2 applied to one input of comparator A4 is predominantly an 800 Hz signal, the amplitude of which is dependent upon the infra-red radiation received by the detector 74. In that regard, since the scanner rotates at 200 cycles per second and four openings 72 are provided therein chopping the radiation four times per revolution, the 800 Hz signal of the filter F2 corresponds to the chopping frequency of the scanner, that is, the frequency at which the scanner chops the infra-red radiation falling on the detector 74.

The second input to the amplifier A4 is a reference voltage provided by resistors R4 and R5 coupled between a positive reference voltage and ground. During the inspection of a bottle having no water therein, the amplitude of the 800 Hz signal on line 106 caused by the repetitive illumination and blocking of illumination from the detector 74 will be substantial, resulting in an output of filter F2 having a peak-to-base amplitude exceeding the reference voltage applied to the other (positive) input of the amplifier A4. This will cause the output of the amplifier A4 to pulse negatively at the rate of 800 Hz, each pulse having a pulse width determined by the period for which the output of filter F2 exceeds the positive input of the amplifier A4. The pulse train output of the amplifier A4 is coupled through resistor R6 to a missing pulse detector 108, the combination of resistor R6 and diode D2 limiting the negative swing of the input to detector 108.

In the preferred embodiment the missing pulse detector is comprised of an integrated circuit generally referred to as a 555 timer connected as shown under the heading "Missing Pulse Detector" on page 6–81 of the publication entitled *Signetics Linear Integrated Circuits*, put out by Signetics of Sunnyvale, Calif. The time delay, as described therein, is chosen to somewhat exceed the period of an 800 Hz signal so that the output of the missing pulse detector will remain in one state so long as an 800 Hz signal is received from amplifier A4, but will change to the opposite state shortly after one, or no more than a few pulses are missing on the input to the detector. In that regard, since the total inspection period corresponds to approximately 1.2 rotations of the scanner, and the infra-red radiation on detector 74 is mechanically chopped four times per scanner rotation, approximately five pulses in the pulse train will be missing during the inspection period for a bottle containing water, caustic solution, etc., though it is preferable to trigger the output on some lesser number of missing pulses. Specifically, when there is a significant amount of water in the bottle being inspected, the amount of infra-red radiation received by detector 74 will be substantially reduced so that the amplitude of the A/C signal on line 106 will also be significantly reduced, resulting in a reduction of the peak-to-base amplitude of the output of filter F2 to a value less than the reference voltage applied to positive input of amplifier A4 and interrupting the pulse input to the missing pulse detector 108 to result in a reject signal to the reject detection logic 102.

In order to provide an adjustment in the sensitivity of the liquid detection portion of the circuitry, the gain of amplifier A2 is made adjustable by a manually adjustable potentiometer P1 in conjunction with resistors R7 and R8 in the feedback circuit of the amplifier. This allows adjustment of the sensitivity to allow the adjustment of the amount of liquid in the container which will be passed by the circuitry. In that regard, the liquid detection is potentially extremely sensitive because of the well known strong absorption characteristics of water when subjected to infra-red radiation of a wavelength for approximately 1.9 microns, and accordingly unless most minimal amounts of moisture in the container are to result in rejection, it has been found desirable to not use too sharp a bandpass filter for the interference filter over the detector to somewhat broaden the wavelength range of the radiation received thereby for sensitivity reduction purposes.

In the preferred embodiment, the particle inspection portion operating on the visible light is comprised of the photovoltaic sensor 68 which provides a signal to amplifier A5. The output of this amplifier is used for two purposes. In particular, foreign matter in the bottom of a bottle may have either of two characteristics, specifically (i), localized foreign matter such as specific objects, drops of paint, etc. and (ii), uniformly distributed foreign matter such as a coating of paint across the entire bottom of the bottle, a uniform layer of other foreign matter, etc. With respect to the inspection for the individual or localized contamination, the output of amplifier A5 is applied to an automatic gain control circuit GC1 which effectively normalizes the average signal, irrespective of variations thereof from bottle to bottle because of bottom thickness, bottle coloring, etc. The output of the automatic gain control circuit is serially coupled to a filter F3, amplifier A6, filter F4, amplifier A7, filter F5, amplifier A8, filter F6 and finally a last amplifier A9. The filters F3 through F6 in the preferred embodiment are passive high pass filters comprised of a series capacitor and resistor to ground, having a time constant of approximately 1 millisecond. Thus, slowly changing signals picked up by detector 68 are grossly attenuated by the filters, though any rapidly changing signal, even though the total amplitude of the change is not large, is essentially directly coupled through the filters to be amplified by the amplifiers to provide a substantial signal to amplifier A9. In that regard, amplifier A9 effectively operates as a comparator with the second input thereto being coupled to a reference voltage determined by resistor R9 and potentiometer P2. For the polarity shown for amplifier A9, so long as the output of filter F6 remains below the reference voltage determined by potentiometer P2 the output of amplifier A9 will remain positive, though when the output of filter F6 exceeds the positive reference voltage on the other input of amplifier A9 the output of the amplifier will change state, thereby signaling a reject signal to the reject detection logic 102. Since the reject signal out of amplifier A9 is dependent upon both the amplitude and the polarity of the signal out of filter F6 for this embodiment, rejection will occur based on a detector signal representing a transition from light to dark (or more accurately, from light to slightly less light representing a partial blockage of the light due to a small item on the bottle bottom), or on the transition from dark to light, but not both in the same system. In the preferred embodiment, polarities of the amplifiers, etc. are set so that rejection occurs on a transition from light to dark. In either case, however, it is to be noted that for this embodiment the rejection signal occurs on a single transition, which of course may represent either of the reflective segments 64 (see FIG. 5) sweeping the portion of the image being blocked by the item in the bottle, so that the inspection period representing approximately 1.2 rotations of the scanner is adequate for the full visual inspection of the bottle bottom.

With respect to the inspection for uniformly dispersed foreign matter on the bottle bottom, the output of amplifier A5 is directly amplified by amplifier A10 and coupled to amplifier A11, also connected as a comparator, the second input of the amplifier being coupled to a a potentiometer P3 for adjustment of the reject level. The potentiometer P3 allows the adjustment to compensate for variations in the light source, bottle thickness, etc., and more importantly for bottle coloring and/or partial opaqueness to visible light.

There has been described herein a new and unique modification of a prior art scanner which provides for the simultaneous inspection of bottles for opaque foreign matter, unilizing visible light, and for aquaeous-base solutions utilizing infra-red light. The system is particularly simple and highly reliable, providing the liquid detection capability at a minimum of increased cost. Obviously while four openings are provided in the scanner so as to chop the infra-red energy falling on the infra-red detector 800 times per second, such a selection was made based upon the manufacturer's recommendations regarding the operating frequency of the detector, and any lessor or greater number of openings may also be used. Similarly, while amplitude detection is used for the liquid detection and rate of change of signal is used for opaque particle detection, other signal conditioning techniques may also be used. Thus, while the present invention has been disclosed and described with respect to a preferred embodiment thereof, it will be understood by those skilled in the art that various changes in form and detail may be made therein without departing from the spirit and scope of the invention.

I claim:

1. Bottle inspection apparatus comprising
   radiation means for directing visible and infrared radiation through the bottom of a bottle to be inspected at an inspection station;
   lens means above said radiation means for focusing visible light passing through the bottle bottom and out through the neck thereof to present an image of the bottom of the bottle at an image plane;
   scanner means located substantially at said image plane, said scanner means having a generally non-reflective background with at least one reflective segment thereon for reflecting a respective portion of an image focused thereon, said scanner means also having at least one opening therethrough;
   a motor for rotating said scanner means at high speed to rotate said reflective segment about a scanner axis to scan the image focused thereon;
   a first detector positioned to receive visible radiation reflected by said scanner means and to provide an electrical signal responsive thereto for sensing the presence of opaque foreign objects in bottles being inspected; and
   a second detector positioned behind said scanner to receive infrared radiation passing through said opening in said scanner and to provide an electrical signal responsive thereto for sensing the presence of an aqueous solution in the bottle.

2. The apparatus of claim 1 further comprised of an interference filter disposed in the path of the radiation incident to said second detector for passing radiation in a selected infrared band.

3. The apparatus of claim 1 wherein said scanner means has a plurality of openings therethrough.

4. The apparatus of claim 3 wherein said second detector is positioned in cooperation with said openings in said scanner to receive infrared light coming from a predetermined region of the bottle bottom.

5. The apparatus of claim 1 further comprised of a rotary transport means for supporting bottles to be inspected adjacent to periphery thereof, and for rotation about the axis of said rotary transport means for transport of bottles in an arc past an inspection station, said second detector and said opening in said scanner means being cooperatively disposed to receive infrared radiation from a region of the bottle bottom generally radially outward from said axis of said rotary transport means.

6. The apparatus of claim 1 further comprised of electronic means for detecting changes in the output of said first and said second detector means.

7. The apparatus of claim 1 further comprised of first electronic means for detecting the amplitude of the alternating signal output of said second detector means to indicate the presence of a water-based solution in a bottle being inspected.

8. The apparatus of claim 7 further comprised of second electronic means for detecting changes in the output of said first detector means to indicate the presence of a localized obstruction to visible light in a bottle being inspected.

9. The apparatus of claim 8 further comprised of third electronic means for detecting the level of output of said first detector means to indicate a bottle having a distributed opaqueness to visible light.

10. Bottle inspection apparatus comprising:
radiation means for directing visible and infrared radiation through the bottom of a bottle to be inspected at an inspection station;
lens means above said radiation means for focusing visible light passing through the bottle bottom and out through the neck thereof to present an image of the bottom of the bottle at an image plane;
scanner means located at said image plane and being rotatable at high speed about a scanner axis slightly inclined with respect to the optical axis defined by said radiation means and said lens means, said scanner means having a generally nonreflective background with at least one reflective segment thereon for reflecting a respective portion of an image focused thereon, said reflective portion having a contour to at least approximately focus the respective portion of an image focused thereon onto a first detector, said scanner means also having at least one opening therethrough generally radially displaced from said scanner axis;
a motor for rotating said scanner means at high speed about said scanner axis to cause said reflective segment to scan the image focused thereon;
a first detector positioned to receive visible radiation reflected by said scanner means and to provide an electrical signal responsive thereto for sensing the presence of opaque foreign objects in bottles being inspected;
a second detector positioned behind said scanner to receive infrared radiation passing through said opening in said scanner and to provide an electrical signal responsive thereto for sensing the presence of an aqueous solution in the bottle.

11. The apparatus of claim 10 further comprised of an interference filter disposed over said second detector for passing radiation in a selected infrared band.

12. The apparatus of claim 10 wherein said scanner means has a plurality of openings therethrough.

13. The apparatus of claim 12 wherein said second detector is positioned in cooperation with said openings in said scanner to receive infrared light coming from a predetermined region of the bottle bottom.

14. The apparatus of claim 10 further comprised of a rotary transport means for supporting bottles to be inspected adjacent the periphery thereof, and for rotation about the axis of said rotary transport means for transport of bottles in an arc past an inspection station, said second detector and said opening in said scanner means being cooperatively disposed to receive infrared radiation from a region of the bottle bottom generally radially outward from said axis of said rotary transport means.

15. The apparatus of claim 10 further comprised of electronic means for detecting changes in the output of said first and said second detector means.

16. The apparatus of claim 10 further comprised of first electronic means for detecting the amplitude of the attenuating signal output of said second detection means to indicate the presence of a water-based solution in a bottle being inspected.

17. The apparatus of claim 16 further comprised of second electronic means for detecting changes in the output of said first detection means to indicate the presence of a localized obstruction to visible light in a bottle being inspected.

18. The apparatus of claim 17 further comprised of third electronic means for detecting the level of output of said first detector means to indicate a bottle having a distributed opaqueness to visible light.

* * * * *

UNITED STATES PATENT AND TRADEMARK OFFICE
CERTIFICATE OF CORRECTION

PATENT NO. : 4,221,961

DATED : Sep. 9, 1980

INVENTOR(S) : Peyton

It is certified that error appears in the above-identified patent and that said Letters Patent is hereby corrected as shown below:

| COLUMN | LINE | |
|---|---|---|
| 1 | 20 | Delete "incorporation", insert --inspection--. |
| 4 | 6 | Delete "3,145,370", insert --3,415,370--. |

Signed and Sealed this

Sixth Day of August 1985

[SEAL]

Attest:

DONALD J. QUIGG

Attesting Officer

Acting Commissioner of Patents and Trademarks